United States Patent [19]

Keim et al.

[11] 4,268,456
[45] May 19, 1981

[54] PROCESS FOR PREPARING CHLOROTHIOLFORMATES

[75] Inventors: William A. Keim; James A. Cook, Jr., both of Barberton, Ohio

[73] Assignee: PPG Industries, Inc., Pittsburgh, Pa.

[21] Appl. No.: 78,328

[22] Filed: Sep. 24, 1979

[51] Int. Cl.³ .................................... C07C 154/00
[52] U.S. Cl. ........................................ 260/455 R
[58] Field of Search .................................. 260/455 R

[56] References Cited

U.S. PATENT DOCUMENTS

| | | | |
|---|---|---|---|
| 2,913,327 | 11/1959 | Tilles et al. | 260/455 R |
| 3,093,537 | 6/1963 | Tilles | 260/455 R |
| 3,126,406 | 3/1964 | Tilles et al. | 260/455 R |
| 3,165,544 | 1/1965 | Tilles | 260/455 R |
| 3,175,897 | 3/1965 | Tilles et al. | 260/455 R |
| 3,185,720 | 5/1965 | Tilles et al. | 260/455 R |
| 3,299,114 | 1/1967 | Tilles | 260/455 R |
| 4,012,405 | 3/1977 | Alesandrini | 260/455 R |
| 4,119,659 | 10/1978 | Alesandrini | 260/455 R |

*Primary Examiner*—John D. Randolph
*Assistant Examiner*—Robert C. Whittenbaugh
*Attorney, Agent, or Firm*—Irwin M. Stein

[57] ABSTRACT

Chlorothiolformates are prepared by reacting a mercaptan with phosgene in the presence of a catalytic amount of a quaternary ammonium salt.

17 Claims, No Drawings

PROCESS FOR PREPARING CHLOROTHIOLFORMATES

CROSS REFERENCE TO RELATED APPLICATIONS

This application is related to commonly assigned, copending U.S. patent applications Ser. No. 60,319, filed July 25, 1979, and Ser. No. 78,329, filed Sept. 24, 1979, which are entitled PROCESS FOR PREPARING CHLOROTHIOLFORMATES.

DESCRIPTION OF THE INVENTION

The catalytic preparation of alkyl and phenyl chlorothiolformates by reaction of the appropriate mercaptan, e.g., an alkyl or phenyl mercaptan, with phosgene has been described in the patent literature. In the absence of catalyst, the reaction can require several days to achieve substantially complete reaction. Exemplary of U.S. patents directed to the preparation of chlorothiolformates are U.S. Pat. Nos. 3,165,544, 3,093,537, 4,012,405 and 4,119,659, which describe the use of activated carbon for the preparation of alkyl and phenyl chlorothiolformates, and U.S. Pat. No. 3,299,114, which describes the use of tertiary amines and heterocyclic amine compounds to catalyze the aforesaid reaction.

It has now been discovered that quaternary ammonium salts can be used to catalyze the reaction of mercaptan with phosgene. In particular, the quaternary ammonium salt can be represented by the general formula, $(R_1R_2R_3R_4N)^+X^-$ wherein $R_1$, $R_2$, $R_3$ and $R_4$ are each selected from the group consisting of $C_1-C_{22}$ alkyl, $C_2-C_8$ alkenyl, phenyl, $C_6-C_9$ alkaryl and $C_6-C_9$ aralkyl, and X is a monovalent anion normally associated with quaternary ammonium salts, such as halogen, hydroxyl, nitrate, methyl sulfate, etc.

DETAILED DESCRIPTION OF THE INVENTION

Certain chlorothiolformates, e.g. ethyl chlorothiolformate, have been found useful as pesticides. See, for example, U.S. Pat. No. 3,093,537 In addition, chlorothiolformates, e.g., ethyl chlorothiolformate, have been found useful as intermediates for the preparation of herbicidally effective thiolcarbamates and similar compounds. See, for example, U.S. Pat. Nos. 2,913,327, 3,126,406, 3,175,897 and 3,185,720. In the latter two patents, chlorothiolformate is reacted further with an amine to produce the corresponding thiolcarbamate.

The present invention relates to the use of quaternary ammonium salt as a catalyst for the reaction of mercaptan with phosgene to produce chlorothiolformates. The reaction can be represented by the following balanced equation:

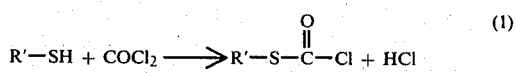

$$R'-SH + COCl_2 \longrightarrow R'-S-\overset{O}{\underset{\|}{C}}-Cl + HCl \quad (1)$$

Quaternary ammonium salts are the products of the final stage of alkylation of nitrogen. The salts can be represented by the formula, $R_{(4)}N^+X^-$, wherein $R_{(4)}$ represents the four organic groups bonded to the nitrogen forming an ion having a positive charge, which is balanced by a negative ion, X. The four organic groups can be varied widely and thus quaternary ammonium salts that can be used in the present process will also vary widely. The more common quaternary ammonium salts that can be used in the present process are represented by the general formula, $(R_1R_2R_3R_4N)^+X^-$, wherein $R_1$, $R_2$, $R_3$ and $R_4$ are each selected from the group consisting of $C_1-C_{22}$ alkyl, $C_2-C_8$ alkenyl, phenyl, $C_6-C_9$ alkaryl and $C_6-C_9$ aralkyl, and X is a monovalent anion normally associated with quaternary ammonium salts. The particular anion associated with the salt depends on the method by which the the quaternary ammonium salt is prepared, e.g., the anion associated with the alkylating agent. Typically, X is a halogen, e.g., chloride, bromide or iodide, hydroxyl, nitrate, methyl sulfate, etc. Regardless of the anion associated with the quaternary ammonium salt initially, it is expected that during use as a catalyst in the present process, the anion will be exchanged for the chloride anion introduced with the phosgene reactant.

The particular aliphatic (saturated or unsaturated, branched or straight chain) or aromatic radical selected for each of the R group of the quaternary ammonium salt, i.e., $R_1$, $R_2$, $R_3$ or $R_4$, can vary. Preferably, one of the R groups is phenyl or aralkyl, one of the groups is a long chain ($C_8-C_{22}$) aliphatic hydrocarbon and two of the groups are shorter chain ($C_1-C_7$) aliphatic groups, and X is a halogen, e.g., chloride ion. In particular, preferred quaternary ammonium salts of the above formula are those in which $R_1$ is a $C_{12}-C_{22}$ alkyl, $R_2$ and $R_3$ are each $C_1-C_{10}$ alkyl, $R_4$ is selected from the group consisting of phenyl and benzyl, and X is chloride. The alkyl groups can be branched or straight chain, and substituted or unsubstituted with functional groups that do not interfer with the catalytic activity of the quaternary ammonium salt.

As examples of $C_1-C_{22}$ alkyl radicals, there can be mentioned methyl, ethyl, n-propyl, isopropyl, n-butyl, isobutyl, secondary butyl, tertiary butyl, n-pentyl, neopentyl, hexyl, neohexyl n-heptyl, n-octyl, 2-ethylhexyl, n-nonyl, n-decyl, undecyl, n-dodecyl, tridecyl, tetradecyl, pentadecyl, hexadecyl, heptadecyl, octadecyl, nonadecyl, eicosyl, heneicosyl and docosyl.

As examples of alkenyl radicals, there can be mentioned; alkyl, methallyl, and butenyl.

Among the $C_6-C_9$ alkaryl and aralkyl radicals, there can be mentioned phenyl, 4-chlorophenyl, 2-tolyl, 3-tolyl, 3-chloro-4-methyl phenyl, 4-bromophenyl, benzyl, 4-chlorobenzyl and 2-phenylethyl.

The quaternary ammonium salts described herein are either commercially available or can be prepared by processes well known in the art. Typically, quaternary ammonium compounds are prepared by the alkylation of primary, secondary or tertiary amines. When primary or secondary amines are used, an alkaline reagent (acid acceptor) is used to neutralize the acid formed by the alkylation. Among the alkylating agents used, methyl halides, e.g., methyl chloride, dimethyl sulfate and benzyl chloride are used most frequently.

Examples of classes of quaternary ammonium salts commercially available include monoalkyl trimethyl quaternaries, dialkyl dimethyl quaternaries, monomethyl trialkyl quaternaries and dimethyl alkyl benzyl quaternaries.

Examples of specific quaternary ammonium salts include: ethyltrimethylammonium iodide, tetramethylammonium chloride, trimethyloctadecylammonium chloride, dimethyldioctadecylammonium chloride, dimethyldicocoammonium chloride, trimethyldodecylammonium chloride, tricaprylylmethylammonium chloride, benzyltrimethylammonium chloride, methylallylphenylbenzylammonium iodide, benzyltriethylammonium chloride, soya trimethyl ammonium chloride, palmityl trimethyl ammonium chloride, coco trimethyl ammonium chloride, allyl trimethyl ammonium chloride, benzyl trimethyl ammonium chloride, dialkyl ($C_{12}$–$C_{18}$) dimethyl ammonium chloride, dialkyl ($C_{14}$–$C_{18}$) dimethyl ammonium chloride, dialkyl ($C_{12}$–$C_{16}$) dimethyl ammonium chloride, distearyl dimethyl ammonium chloride, trialkyl ($C_8$–$C_{18}$) monomethyl ammonium chloride, dimethyl alkyl ($C_{12}$–$C_{16}$) benzyl ammonium chloride, dimethyl alkyl ($C_{10}$–$C_{18}$) benzyl ammonium chloride, and dimethyl stearyl benzyl ammonium chloride.

The skilled artisan will recognize that quaternary ammonium salts other than described above are commercially available or can be routinely prepared. Typical commercial combinations include methyl groups, fatty alkyls, imidazolinium and amido amine substituents along with chloride or methyl sulfate anions. In the above specific salts, it is recognized that ethyl or propyl can be substituted for methyl, and hydroxyl or bromo substituted for the chloro anion. Such quaternary ammonium salts can be used as the catalyst for the process described herein and it is expected that results similar to that of the Example will be obtained.

The amount of quaternary ammonium salt used to catalyze the reaction of mercaptan with phosgene is that amount which is required to accelerate the reaction to commercially acceptable rates, i.e., a catalytic amount. Whereas several days may be required to accomplish significant conversions of mercaptan, e.g., greater than 80 percent conversion, in the absence of catalyst, such conversions can be accomplished within 0.1 to 20 hours with use of a quaternary ammonium salt. Typically, between about 10 and about 0.01 mole percent of quaternary ammonium salt, based on the mercaptan, can be used. More commonly, between about 0.1 and about 1 or 5 mole percent of quaternary ammonium salt is used. It has been found, for example, that about 0.2 mole percent of benzyltriethylammonium chloride, based on mercaptan, catalyzes the reaction of ethyl mercaptan with phosgene at economical rates and yields the corresponding chlorothiolformate of high quality.

The quaternary ammonium salt can be added to the reactor in any convenient manner, e.g., before, after or simultaneously with one or both of the reactants. In a preferred embodiment, the ammonium salt is added to a pool of phosgene previously formed in the reactor.

Mercaptans that can be reacted with phosgene in the presence of quarternary ammonium salt catalyst can be represented by the formula, R'—SH, wherein R' is alkyl, cycloalkyl, cycloalkylmethyl, lower alkenyl, aryl, alkaryl, aralkyl, haloaryl, haloaralkyl, and carboalkoxy alkyl. Such mercaptans are well recognized in the art, as can be seen by reference to the aforesaid described U.S. patents. Mercaptans, such as those described herein, can be prepared by methods known in the art. Among the methods described in the art for preparing mercaptans are the reaction of an alkali alkyl sulfate or alkyl halide with sodium or potassium hydrosulfide; the vapor phase reaction of the appropriate alcohol with hydrogen sulfide; and the addition of hydrogen sulfide to the appropriate unsaturated organic compound.

Typically, R' in the formula R'-SH is a branched or straight chain $C_1$–$C_{15}$ alkyl, $C_2$–$C_5$ alkenyl, $C_3$–$C_7$ cycloalkyl or cycloalkylmethyl, $C_6$–$C_{10}$ aryl, $C_6$–$C_{10}$ alkaryl or aralkyl, $C_6$–$C_{10}$ haloaryl or haloaralkyl, or $C_2$–$C_{10}$ carboalkoxyalkyl radical. The halo prefix in the aforesaid radicals includes the halogen substituents, i.e., chloro, bromo, fluoro and iodo, preferably chloro and bromo. Generally the aliphatic and aromatic radicals described with respect to the secondary amine are also suitable as substituents for the R' group of the mercaptan. More typically, R' is a $C_1$–$C_{10}$, preferably $C_1$–$C_6$ alkyl, $C_3$–$C_4$ alkenyl, $C_5$–$C_6$ cycloalkyl or cycloalkylmethyl, phenyl, $C_1$–$C_4$ alkyl substituted phenyl, chlorophenyl including mono- and polychlorinated phenyl, benzyl and chlorobenzyl, including mono- and polychlorinated benzyl, or $C_2$–$C_5$ carboalkoxyalkyl radical.

Examples of organic mercaptans which can be suitably used in the reaction of the present invention are alkyl mercaptans such as methylmercaptan, ethylmercaptan, isopropylmercaptan, n-propylmercaptan, isobutylmercaptan, secondary butylmercaptan, n-butylmercaptan, 2-pentylmercaptan, neopentylmercaptan, n-pentylmercaptan, n-hexylmercaptan, neohexylmercaptan, n-heptylmercaptan, n-octylmercaptan, and the like. As examples of cycloalkyl mercaptans, the following can be mentioned: cyclopentylmercaptan, cyclohexylmercaptan, 2-methylcyclohexylmercaptan, 3-methylcyclohexylmercaptan, cyclopropylmethylmercaptan, cyclopentylmethylmercaptan, cyclohexylmethylmercaptan, and the like. Allyl mercaptan and butenyl mercaptan are typical examples of lower alkenyl mercaptans that can be used in the above defined reaction.

Also useful are aryl, alkaryl, aralkyl, haloaryl and haloaralkyl compounds exemplified by the following compounds: mercaptobenzene, 2-mercaptonaphthalene, 4-mercaptotoluene, 2-mercaptotoluene, 3-mercaptotoluene, 2,4-dimethylmercaptobenzene, 2,5-dimethylmercaptobenzene, 4-tert-butyl-mercaptobenzene, 1-methyl-2-mercaptonaphthalene, 4-ethylmercaptobenzene, benzylmercaptan, mercaptoethyl benzene, mercaptopropyl benzene, triphenylmethyl mercaptan, mercaptomethyl naphthalene, mercaptoethyl naphthalene, mercaptobutyl naphthalene, 2-chloromercaptobenzene, 3-chloromercaptobenzene, 4-chloromercaptobenzene, 2,5-dichloromercaptobenzene, 4-bromomercaptobenzene, 2-iodomercaptobenzene, 3-iodomercaptobenzene, 4-iodomercaptobenzene, 2-chlorobenzylmercaptan, 3-chlorobenzylmercaptan, 4-chlorobenzylmercaptan, 2,4-dichlorobenzylmercaptan, 3,4-dichlorobenzylmercaptan, 4-bromobenzylmercaptan, 4-chloro-1-mercaptonaphthalene, 4-bromo-1-mercaptonaphthalene, and the like. Similarly, examples of carboalkoxyalkyl mercaptans that can be reacted with phosgene according to the present invention are those compounds typified as esters of mercapto-acids. Suitable examples are methyl mercaptoacetate, ethyl mercaptoacetate, propyl mercaptoacetate, butyl mercaptoacetate, pentyl mercaptoacetate, hexyl mercaptoacetate, methyl 2-mercaptopropionate, ethyl 2-mercaptopropionate, pentyl 2-mercaptopropionate, methyl 3-mercaptopropionate, ethyl 3-mercaptopropionate, hexyl 3-mercaptopropionate, methyl 2-mercaptobutyrate, propyl 2-mercaptobutyrate, hexyl 2-mercaptobutyrate, methyl 3-mercaptobutyrate, ethyl 3-mercaptobutyrate, hexyl 3-mercaptobutyrate, methyl 4-mercaptobutyrate, ethyl 4-mercaptobutyrate, hexyl 4-mercaptobutyrate, methyl 3-mercaptovalerate, ethyl 3-mercaptovalerate, hexyl 3-mercaptovalerate, methyl 5-mercaptovalerate, ethyl 5-mercaptovalerate, hexyl 5-mercaptovalerate, and the like.

The amount of phosgene used in the reaction can vary; but is typically at least a stoichiometric amount based on equation (1). That is, at least one mole of phosgene is used for every mole of mercaptan. More usually, an excess of phosgene, e.g., from about 5 to about 50 mole percent excess phosgene, based on the mercaptan is used for the reasons that the phosgene can be removed more readily from the reaction mixture and an excess of mercaptan favors the production of by-product dithiolcarbonate. However, if the presence of dithiolcarbonate can be tolerated, the amount of phosgene used can be less than a stoichiometric amount, i.e., the mercaptan is used in excess.

Reaction of the mercaptan with phosgene is commonly conducted at atmospheric pressure, although subatmospheric or superatmospheric pressures can be used. Reaction temperatures should be maintained as low as possible, consonant with reasonable reaction rates since, at high temperatures, by-product dithiolcarbonate can be formed in significant amounts. Since the mercaptans and chlorothiolformates described hereinbefore exhibit varying reactivities and varying decomposition temperatures such factors must be taken into account in selecting the reaction temperature. Commonly, reaction temperatures will be less than about 70° C. With an excess of phosgene, the reaction temperature will typically range between about 0° C. and about 70° C. at atmospheric pressure and with refluxing phosgene. More typically, reaction temperatures will range between about 10° C. and about 50° C., e.g., between 10° C. and 35° C.

The reactants can be introduced into a suitable reactor in any order or simultaneously; however, it is preferable to add the mercaptan to a pool of phosgene. Further, when carrying out the process on a batch or semi-continuous basis, it is preferred that the mercaptan be added slowly to the pool of phosgene so as to control the heat of reaction and minimize the formation of by-product dithiolcarbonate. When phosgene is added to a pool of mercaptan, the reaction commences at a higher temperature than when the order of reactant introduction is reversed, thereby increasing the opportunity for formation of by-product dithiolcarbonate.

The reaction can be conducted batch-wise or semi-continuously also by introducing the reactants to a heel of the chlorothiolformate, i.e., a portion of the reaction product of a previous preparation containing the catalyst. Although the initial reaction temperature is higher than when mercaptan is added to a pool of phosgene, reaction times are shorter. Preparation of the chlorothiolformate by a continuous reaction is also contemplated.

The chlorothiolformate product prepared in accordance with the present process contains low levels of organic disulfide, i.e., R'—S—S—R', and dithiolcarbonate by-products. The low level of disulfide impurity is in contrast to the significant quantities of such impurity that is found in chlorothiolformate prepared using activated carbon as the catalyst. See, for example, U.S. Pat. No. 4,012,405 (column 1) wherein from 3 to 7 percent of diethyl disulfide is produced during preparation of ethyl chlorothiolformate by reaction of ethyl mercaptan with phosgene in the presence of activated carbon catalyst. Further, the quaternary ammonium salt of the present process does not appear to catalyze the reaction of the chlorothiolformate with further mercaptan to produce the dithiolcarbonate by-product.

In conducting the reaction of the present process, the reaction mixture is usually agitated to assist in removing heat from the reactor. At the end of the reaction, excess phosgene is removed, e.g., by stripping. Phosgene can be stripped from the chlorothiolformate product by pulling a vacuum on the system—thereby permitting the phosgene to boil off; passing an inert gas, e.g., nitrogen or argon, through the reaction mixture; or, heating the reaction mixture slightly to boil off the excess phosgene. Upon removal of the excess phosgene, the quaternary ammonium salt catalysts can be removed from the chlorothiolformate by filtration or washing with water. The latter is not preferred because water can react with the chlorothiolformate, thereby decreasing the yield of product. The catalyst can be left in the product also.

If the chlorothiolformate product is to be converted to a thiolcarbamate, secondary amine is mixed with the chlorothiolformate product in the presence of an acid acceptor, e.g., sodium hydroxide, in amounts sufficient to convert the thiolformate to the corresponding thiolcarbamate. The secondary amine can be represented by the formula, $R_5R_6NH$, wherein $R_5$ and $R_6$ are selected from the group consisting of $C_2$–$C_4$ alkyl, cyclohexyl, and allyl, e.g., diethylamine, di-n-propylamine, di-n-butylamine, di-isobutylamine, ethyl cyclohexylamine, and di-allylamine.

The degassed chlorothiolformate product is obtained in sufficient purity to be used in most commercial applications, e.g., as an intermediate for the preparation of thiolcarbamates. If further purification is desired, the chlorothiolformates can be distilled or recrystallized from a suitable solvent to obtain a more pure product.

In a typical embodiment of a batch process, about 0.2 mole percent of quaternary ammonium salt (based on mercaptan) is introduced into the reactor. Thereafter, 0.6 mole of phosgene, per mole of mercaptan, used is condensed in the reactor to establish a pool of phosgene at about 10° C. Mercaptan is then added to the reactor together with the further addition of about 0.6 mole of phosgene per mole of mercaptan used. The additional phosgene and mercaptan reactant are added to the reactor over a period of about one hour and the reaction maintained under constant agitation. Vaporized phosgene is condensed in a reflux condenser connected to the reactor and condensed phosgene returned to the reactor. As the reaction takes place, the phosgene and mercaptan are consumed and the boiling point of the reaction mixture rises, e.g., from about 10° C. to about 27° C. when using ethyl mercaptan. At the end of about 10 hours, excess phosgene and unreacted mercaptan are stripped from the reactor by degassing, and the chlorothiolformate product removed from the reactor.

The present invention is more particularly described in the following examples which are intended as illustrative only since numerous modifications and variations therein will be apparent to those skilled in the art. In the examples, the purity of the chlorothiolformate product is reported as peak area percent, i.e., by estimating the area under the peaks of the chart produced by gas liquid chromatographic analysis.

EXAMPLE I 0.6 grams (0.2 mole percent) of solid benzyltriethylammonium chloride was charged to a one liter, round bottom, three-neck flask containing about 100 grams of ethyl chlorothiolformate. The flask was equipped with a stirrer and motor, thermometer, addition funnel, phosgene inlet tube and a dry ice-acetone condenser and cooled with a wet ice bath. Thereafter, 1.37 moles of phosgene were condensed into the flask. Seventy-five grams (1.208 moles) of ethyl mercaptan was placed in the addition funnel and added to the reaction flask in about 38 minutes with stirring. The temperature in the reaction flask at the start of ethyl mercaptan addition was 21° C. The ice bath was not used during the addition of the ethyl mercaptan. The temperature of the reaction mixture at the end of the addition of ethyl mercaptan was 17° C. The reaction mixture was stirred for about 11 hours during which time 5 samples were taken and analyzed by means of gas liquid chromatographic analysis (GLC) of the unreacted mercaptan. The reaction mixture was stirred overnight (an additional 9 hours) at which time a further sample was taken. The temperature of the reaction mixture was maintained at 20° C. during the reaction. Analysis of the six samples taken was tabulated in Table I.

TABLE I

| Sample No. | Elapsed Time, Minutes | Peak Area Percent, Compounds[b] | | | |
|---|---|---|---|---|---|
| | | $COCl_2$ | ETSH | ECTF | DETC |
| 1 | 0[a] | 35 | 25 | 39 | 0.1 |
| 2 | 45 | 26 | 17 | 57 | 0.1 |
| 3 | 150 | 14 | 11 | 75 | 0.3 |
| 4 | 330 | 8 | 6 | 85 | 0.1 |
| 5 | 670 | 5 | 3 | 91 | 0.1 |
| 6 | 1330 | 3 | 2 | 95 | 0.1 |

[a]17 minutes after all ETSH added to reaction flask.
[b]$COCl_2$ - phosgene
ETSH - ethyl mercaptan
ECTF - ethyl chlorothiolformate
DETC - diethyl dithiolcarbonate Additional phosgene (1.01 moles) and 50 grams (0.81 moles) of ethyl mercaptan were added all at once to the reaction flask containing the aforesaid reaction product. The temperature of the reaction mixture was about 20° C. The reaction mixture was stirred for about 9½ hours during which time 4 samples were taken. The reaction mixture was stirred overnight (an additional 14 hours) and a final sample taken. The reaction mixture was maintained during this period at 20° C. Results are tabulated in Table II.

TABLE II

| Sample No. | Elapsed Time, Minutes | Peak Area Percent, Compounds[b,c] | | | |
|---|---|---|---|---|---|
| | | $CoCl_2$ | ETSCH | ECTF | DETC |
| 1 | 0 | 22 | 15 | 62 | 0.1 |
| 2 | 90 | 16 | 10 | 73 | 0.1 |
| 3 | 270 | 11 | 6 | 83 | 0.1 |
| 4 | 570 | 8 | 3 | 90 | 0.1 |
| 5 | 1410 | 5 | 1 | 94 | 0.1 |

[c]Traces of diethyl disulfide were also found.

The data of Tables I and II show that quaternary ammonium salt, e.g., benzyltriethylammonium chloride, catalyze the reaction of phosgene with mercaptan, e.g., ethyl mercaptan, to form chlorothiolformate. After 5-6 hours, the reaction mixture was found to be at least about 85 percent ethyl chlorothiolformate. After 10-11 hours, the reaction mixture was found to contain at least 90 percent chlorothiolformate.

EXAMPLE II (COMPARATIVE)

Into a 30 milliliter serum bottle, with a Viton septum cap, was placed 24.5 grams (0.248 mole) of phosgene and 12.0 grams (0.193 mole) of ethyl mercaptan. The mixture was held at 0° C. and 1.0 grams (0.01 mole) of triethylamine was added to the bottle. The mixture was stirred and held at 0° C. for 4.5 hours and the reaction followed by GLC analysis. In the aforesaid 4.5 hours, approximately 80 percent of the ethyl mercaptan disappeared and ethyl chlorothiolformate was found.

In a similar serum bottle was placed 21.0 grams (0.212 mole) of phosgene, 9.6 grams (0.155 mole) of ethyl mercaptan and 0.56 grams (0.01 mole) of ammonium chloride. The ammonium chloride did not dissolve to a significant extent. The reaction mixture was held at room temperature (about 23° C.) for 4 hours and at least 80 percent of the ethyl mercaptan remained unreacted at the end of that time period.

It was concluded from the data of this example that ammonium chloride was at best a poor catalyst for the reaction of ethyl mercaptan with phosgene.

While the present invention has been exemplified by ethyl mercaptan and benzyltriethylammonium chloride, other of the above described mercaptans or quaternary ammonium salts can be substituted for the ethyl mercaptan and benzyltriethylammonium chloride respectively of the exemplification and expect to obtain the corresponding chlorothiolformate.

Although the present process has been described with reference to specific details of certain embodiments thereof, it is not intended that such details should be regarded as limitations upon the scope of the invention except as and to the extent that they are included in the accompanying claims.

We claim:

1. In the process of preparing organic chlorothiolformate by reaction of an organic mercaptan having the formula R'—SH with phosgene, wherein R' is alkyl, cycloalkyl, cycloalkylmethyl, lower alkenyl, aryl, alkaryl, aralkyl, haloaryl, haloaralkyl, carboalkoxy alkyl, the improvement which comprises conducting said reaction in the presence of a catalytic amount of a quaternary ammonium salt of the formula:

$$(R_1R_2R_3R_4N)^+X^-$$

wherein $R_1$, $R_2$, $R_3$ and $R_4$ are each selected from the group consisting of $C_1$-$C_{22}$ alkyl, $C_2$-$C_8$ alkenyl, phenyl, $C_6$-$C_9$ alkaryl, and $C_6$-$C_9$ aralkyl, and X is a monovalent anion normally associated with quaternary ammonium salts.

2. The process of claim 1 wherein the anion, X, is chloride, bromide or hydroxyl.

3. The process of claim 1 wherein from 0.01 to 10 mole percent of quaternary ammonium salt, based on the mercaptan, is used.

4. The process of claim 3 wherein from 0.1 to 5 mole percent of quaternary ammonium salt is used.

5. The process of claim 1 wherein $R_1$, $R_2$, $R_3$ and $R_4$ are each selected from the group consisting of $C_1$-$C_{22}$ alkyl, allyl, phenyl and benzyl, and X is chloride, bromide or hydroxyl.

6. The process of claim 1 wherein $R_1$ is a $C_{10}$-$C_{22}$ alkyl, $R_2$ and $R_3$ are each $C_1$-$C_{12}$ alkyl, $R_4$ is selected from the group consisting of phenyl and benzyl, and X is chloride.

7. The process of claim 1 wherein R' is a $C_1$-$C_{15}$ alkyl, $C_2$-$C_5$ alkenyl, $C_3$-$C_7$ cycloalkyl or cycloalkylmethyl, $C_6$-$C_{10}$ aryl, $C_6$-$C_{10}$ alkaryl or aralkyl, $C_6$-$C_{10}$ haloaryl or haloaralkyl, or $C_2$-$C_{10}$ carboalkoxyalkyl radical.

8. The process of claim 1 wherein R' is a $C_1$-$C_{10}$ alkyl, $C_3$-$C_4$ alkenyl, $C_5$-$C_6$ cycloalkyl or cycloalkylmethyl, phenyl, $C_1$-$C_4$ alkyl substituted phenyl, or benzyl radical.

9. The process of claim 1 wherein from about 5 to about 50 mole percent excess phosgene is used.

10. In the process of preparing alkylchlorothiolformate by reacting an alkyl mercaptan having the formula R'—SH, wherein R' is a $C_1$–$C_6$ alkyl, with phosgene, the improvement which comprises conducting said reaction in the presence of a catalytic amount of a quaternary ammonium salt having the formula $(R_1R_2R_3R_4N)^+X^-$ wherein $R_1$ is a $C_{10}$–$C_{22}$ alkyl, $R_2$ and $R_3$ are each $C_1$–$C_{12}$ alkyl, $R_4$ is selected from the group consisting of phenyl and benzyl, and X is chloride.

11. The process of claim 10 wherein between 0.01 and 10 mole percent of quaternary ammonium salt, based on the mercaptan, is used.

12. The process of claim 10 or 11 wherein R' is ethyl or propyl.

13. The process of claim 10 or 11 wherein from about 5 to about 50 mole percent excess phosgene is used.

14. A process which comprises reacting an organic mercaptan having the formula, R'—SH, wherein R' is a $C_1$–$C_6$ alkyl, with phosgene, said phosgene being present in amounts of from about 5 to about 50 mole percent excess, in the presence of a catalytic amount of quaternary ammonium salt having the formula, $(R_1R_2R_3R_4N)^+X^-$, wherein $R_1$ is a $C_{10}$–$C_{22}$ alkyl, $R_2$ and $R_3$ are each $C_1$–$C_{12}$ alkyl, $R_4$ is selected from the group consisting of phenyl and benzyl and X is chloride, to thereby produce a reaction product comprising the corresponding alkyl chlorothiolformate, degassing the reaction product to remove excess phosgene, and reacting secondary amine of the formula, $R_5R_6NH$, wherein $R_5$ and $R_6$ are each selected from the group consisting of $C_2$–$C_4$ alkyl, cyclohexyl and allyl, with the degassed reaction product in amounts sufficient to convert the alkyl chlorothiolformate to the corresponding alkyl thiolcarbamate.

15. The process of claim 14 wherein from 0.01 to 10 mole percent of quaternary ammonium salt is used.

16. The process of claim 15 wherein R' is ethyl or propyl and $R_5$ and $R_6$ are each selected from the group consisting of $C_2$–$C_4$ alkyl, cyclohexyl and allyl.

17. The process of claim 16 wherein the secondary amine is selected from the group consisting of diethylamine, di-n-propylamine, di-n-butylamine, di-isobutylamine, ethyl cyclohexylamine, and di-allylamine.

* * * * *